United States Patent
Kokenis

(10) Patent No.: US 8,936,562 B2
(45) Date of Patent: Jan. 20, 2015

(54) EZ EARS

(71) Applicant: Louis J. Kokenis, Arnold, MO (US)

(72) Inventor: Louis J. Kokenis, Arnold, MO (US)

(73) Assignee: EZ Ears, LLC, Arnold, MO (US)

( * ) Notice: Subject to any disclaimer, the term of this patent is extended or adjusted under 35 U.S.C. 154(b) by 0 days.

(21) Appl. No.: 13/762,676

(22) Filed: Feb. 8, 2013

(65) Prior Publication Data

US 2013/0237920 A1    Sep. 12, 2013

Related U.S. Application Data

(60) Provisional application No. 61/608,201, filed on Mar. 8, 2012.

(51) Int. Cl.
| | |
|---|---|
| *A61M 35/00* | (2006.01) |
| *A61M 31/00* | (2006.01) |
| *A61F 9/00* | (2006.01) |
| *A61F 11/00* | (2006.01) |
| *A01K 13/00* | (2006.01) |
| *A61M 3/02* | (2006.01) |
| *A61D 7/00* | (2006.01) |

(52) U.S. Cl.
CPC .............. *A61M 3/0279* (2013.01); *A61D 7/00* (2013.01); *A61M 3/0258* (2013.01); *A61M 2210/0662* (2013.01)
USPC ................ 604/2; 604/275; 606/162; 119/600

(58) Field of Classification Search
CPC ....... A61F 11/006; A61F 13/38; A61F 11/00; A61M 35/006; A61M 2210/0662; A61M 35/003; A61M 31/00
USPC ........... 604/1–3, 275–276; 119/600; 606/162
See application file for complete search history.

(56) References Cited

U.S. PATENT DOCUMENTS

| | | | |
|---|---|---|---|
| 3,938,898 A * | 2/1976 | Reitknecht | 401/183 |
| 4,225,254 A | 9/1980 | Holberg et al. | |
| 6,187,021 B1 | 2/2001 | Wim | |
| 6,386,781 B1 * | 5/2002 | Gueret | 401/198 |
| 6,432,117 B1 * | 8/2002 | Murray | 606/162 |
| 7,500,981 B1 | 3/2009 | Jubrail | |
| 7,784,427 B2 | 8/2010 | Weinblatt | |
| 2003/0152414 A1 | 8/2003 | Yu | |
| 2003/0187469 A1 | 10/2003 | Olson | |
| 2009/0124985 A1 * | 5/2009 | Hasenoehrl et al. | 604/289 |
| 2011/0160635 A1 * | 6/2011 | Baschnagel | 604/2 |

* cited by examiner

*Primary Examiner* — Rebecca E Eisenberg
(74) *Attorney, Agent, or Firm* — Buckingham, Doolittle & Burroughs, LLC

(57) ABSTRACT

A pet ear cleaning device is disclosed for gently cleaning an animal's ears. The device can be used for home or veterinary use. The pet ear cleaning device comprises a nozzle, a liquid reservoir in fluid communication with the nozzle, an internal pump assembly, and a tip for cleaning a pet's ear. A user would press a manual dispensing component which would activate the internal pump assembly which would then draw fluid from the liquid reservoir and transfer it to the nozzle. The liquid reservoir is typically a reusable reservoir that a user would re-fill with ear cleaning solution when empty, or it can be a replacement cartridge. Further, the nozzle typically comprises threads on its end for retaining the cleaning tip on the nozzle. After use, a user would discard the tip via a manually operated discard component that allows a user to remove the soiled tip hands free.

15 Claims, 4 Drawing Sheets

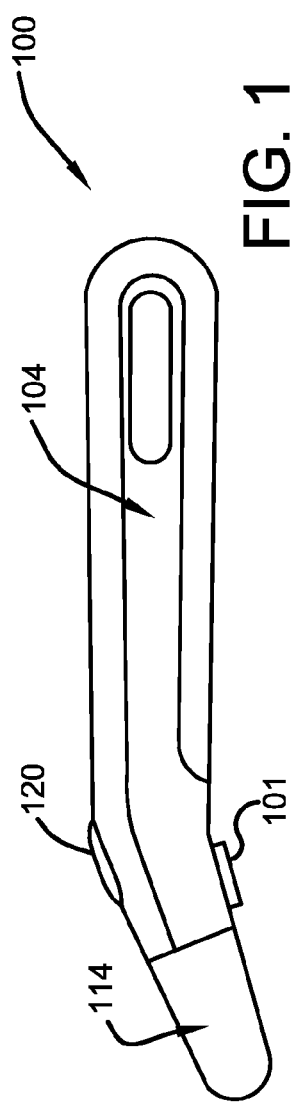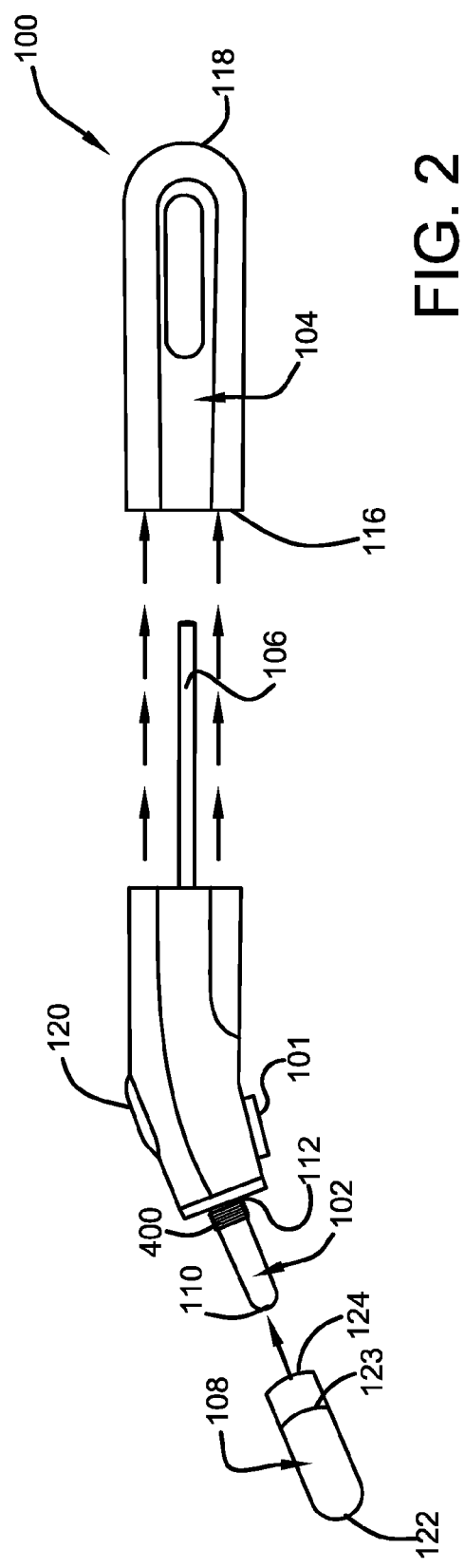

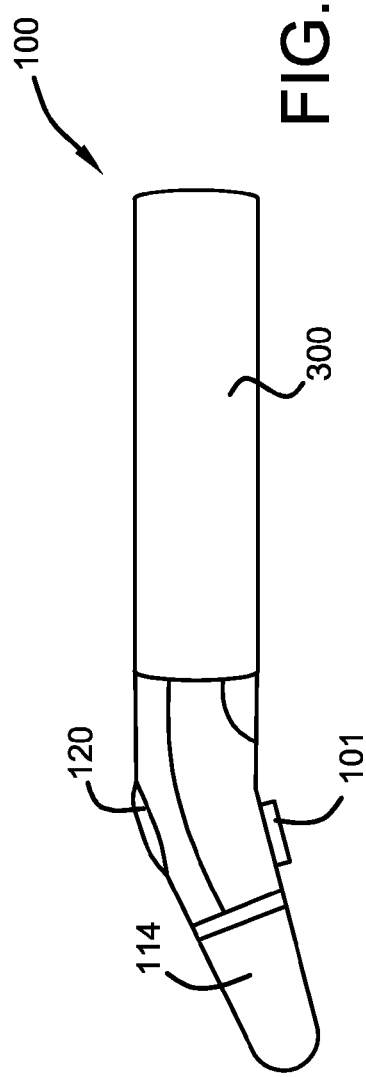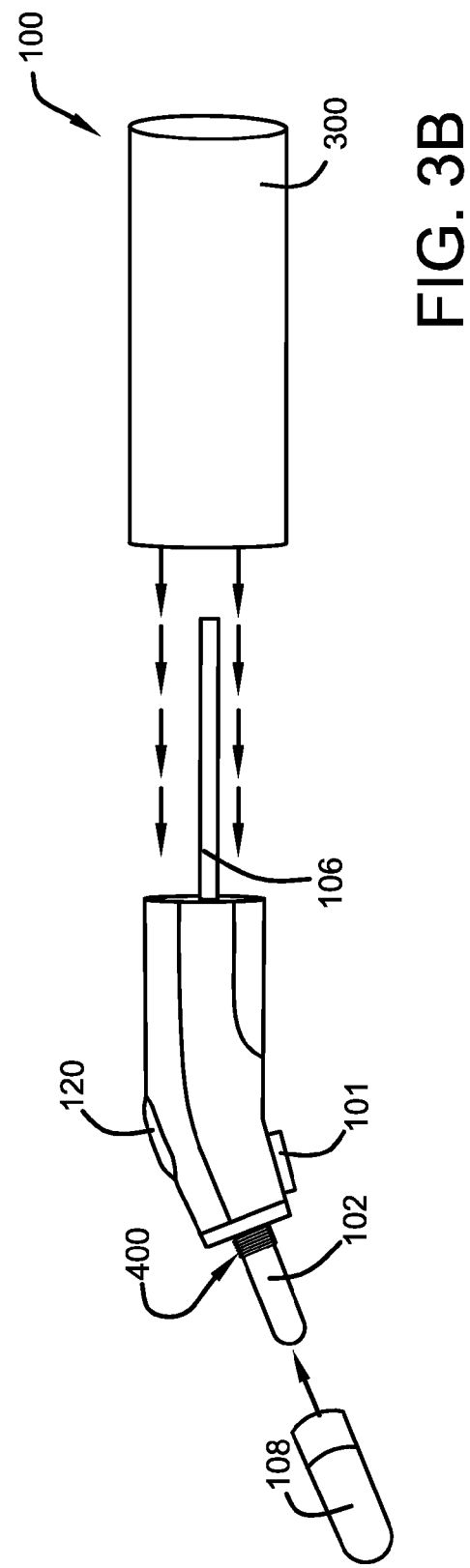

EZ EARS

CROSS-REFERENCE

This application claims priority from Provisional Patent Application Ser. No. 61/608,201 filed Mar. 8, 2012.

BACKGROUND

If pet owners do not properly clean their pets' ears, the animals may develop ear mites or an ear infection, which can be uncomfortable, emit a fowl odor, and lead to a costly trip to the veterinarian. The traditional methods of pet ear cleaning can be messy. For example, traditional methods typically involve squirting liquid into the pet's ear. Then, a user has to use his or her finger and a cotton ball to clean the inside of the pet's ear. As a result, the user typically ends up with dirty fingers, messy cotton balls, and liquid on the floor or other surfaces. In addition, traditional methods of pet ear cleaning can be uncomfortable for the animal. For example, the liquid squirted in the pet's ears tends to startle them and can cause the pets to pull away, or even snap at the owner. An effective solution to prevent these problems is necessary.

There is a need for a pet ear cleaning device that can gently clean an animal's ears. The pet ear cleaning device includes a liquid release mechanism (such as a pump), a main chamber for the ear cleaning solution, and a disposable foam or cotton tip. This unique device may be appreciated by pet owners for its ease of use, and appreciated by pets for the comfortable ear cleaning experience it provides.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises a pet ear cleaning device used to gently clean an animal's ears, the device can be used for home or professional (i.e., veterinary) use. The pet ear cleaning device preferably comprises a nozzle, a liquid reservoir in fluid communication with the nozzle, an internal pump assembly, and a disposable tip for cleaning a pet's ear. Typically, the interior of the nozzle houses a tube that extends down into the liquid reservoir. The tube functions to draw fluid from the liquid reservoir via the internal pump assembly, and then transfers it to the nozzle to be released. A user would press a manual dispensing component which would activate the internal pump assembly which would then draw fluid from the liquid reservoir and transfer it to the nozzle. The liquid reservoir is typically a reusable reservoir that a user would re-fill with ear cleaning solution when empty. Further, the nozzle typically comprises threads on its end for retaining the cleaning tip on the nozzle.

In a preferred embodiment, the liquid reservoir can be a replacement cartridge. A user would take the pre-filled replacement cartridge and remove the lid, usually by unscrewing it. A user then would attach the pre-filled replacement cartridge onto the nozzle and would secure it thereto. Typically, the replacement cartridge would be screwed onto the nozzle. Once secure, the pet ear cleaning device would be used as normal to clean a pet's ears.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

FIG. 1 illustrates a perspective view of the pet ear cleaning device in accordance with the disclosed architecture.

FIG. 2 illustrates a perspective view of the pet ear cleaning device with the foam tip and the liquid reservoir removed in accordance with the disclosed architecture.

FIG. 3A illustrates a perspective view of the pet ear cleaning device with a replacement cartridge in accordance with the disclosed architecture.

FIG. 3B illustrates a perspective view of the pet ear cleaning device with the foam tip and the replacement cartridge removed in accordance with the disclosed architecture.

DESCRIPTION OF PREFERRED EMBODIMENTS

Figure 4:
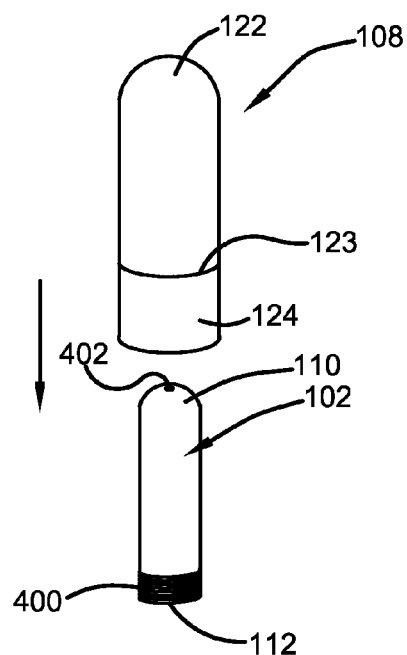
FIG. 4 illustrates a perspective view of how the foam tip fits over the nozzle of the pet ear cleaning device in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

The present invention discloses a pet ear cleaning device that can gently clean an animal's ears. The device simplifies the cleaning process for owners, as traditional methods of pet ear cleaning can be messy and uncomfortable for the animal. Thus, the disclosed device may be appreciated by pet owners for its ease of use, and appreciated by pets for the comfortable ear cleaning experience it provides.

In one embodiment, the pet ear cleaning device comprises a nozzle, a liquid reservoir in fluid communication with the nozzle, an internal pump assembly, and a disposable tip for cleaning a pet's ear. A user would press a manual dispensing component which would activate the internal pump assembly which would then draw fluid from the liquid reservoir and transfer it to the nozzle and the cleaning tip. The liquid reservoir is typically a reusable reservoir that a user would re-fill with ear cleaning solution when empty or, in a preferred embodiment, it can be a replacement cartridge. Further, the nozzle typically comprises threads at its end for retaining the cleaning tip on the nozzle.

Referring initially to the drawings, FIGS. 1-2 illustrate the pet ear cleaning device 100 used to gently clean an animal's ears, the device 100 can be used for home or professional (i.e., veterinary) use. The pet ear cleaning device 100 comprises a nozzle or spray tip 102, a liquid reservoir 104 in fluid communication with the nozzle 102, an internal pump assembly and tube 106, and a tip 108 for cleaning a pet's ear.

The nozzle 102 comprises a first end 110 and a second end 112. Typically, the nozzle 102 is cylindrical in shape, however any other suitable shape can be used as is known in the art without affecting the overall concept of the invention. The nozzle 102 would generally be constructed of polyvinyl chloride (PVC), acrylonitrile butadiene styrene (ABS), or any other similar polymer, etc., though any other suitable material may be used to manufacture the nozzle 102 as is known in the art without affecting the overall concept of the invention. The nozzle 102 can also comprise a variety of colors and designs to suit user and manufacturing preference. The nozzle 102 is approximately between 1.0 and 1.25 inches long as measured from the first end 110 to the second end 112, and approximately between 5.0 millimeters and 7.0 millimeters in diameter.

Typically, the nozzle 102 is hollow, but it does not have to be and can function by being partly solid. Additionally, the interior of the nozzle 102 houses a tube 106 that extends down into the liquid reservoir 104. The tube can be a standard pump tube as is known in the art and functions to draw fluid from the liquid reservoir 104 to the nozzle 102, to then be released by the nozzle 102. Further, the nozzle 102 typically comprises threads on its second end 112 for retaining the tip 108 on the nozzle 102, or other suitable securing means for retaining the tip 108 as is known in the art such as grip rings, snap rings, o-rings, or the like. Additionally, the nozzle 102 can comprise a dust cap 114 to protect the nozzle 102 when the device 100 is not in use. Once the tip 108 is removed, the dust cap 114 is secured to the nozzle 102 via the threads or other suitable securing means. Thus, during use the tip 108 for cleaning a pet's ear can be secured to the nozzle 102 via the threads, and when the device 100 is not in use, the tip 108 is removed and the dust cap 114 is secured to the nozzle 102 via the threads.

The pet ear cleaning device 100 further comprises a liquid reservoir 104 comprising a first end 116 and a second end 118. The first end 116 of the liquid reservoir 104 is secured to the second end 112 of the nozzle 102 via any suitable securing means as is known in the art, such as welding, gluing, threading, etc., and is in fluid communication with the nozzle 102. Typically, the liquid reservoir 104 is cylindrical in shape, however any other suitable shape can be used as is known in the art without affecting the overall concept of the invention. Further, the liquid reservoir 104 would generally be constructed of the same materials as the nozzle 102, such as PVC, ABS, or any other similar polymer, etc., though any other suitable material may be used to manufacture the liquid reservoir 104 as is known in the art without affecting the overall concept of the invention. The liquid reservoir 104 can also comprise a variety of colors, logos, and designs to suit user and manufacturing preference. The liquid reservoir 104 is approximately between 3.0 and 4.0 inches long as measured from the first end 116 to the second end 118, and approximately between 1.0 and 1.25 inches in diameter.

Typically, the liquid reservoir 104 is hollow, but it does not have to be and can function by being partly solid, as long as the liquid reservoir 104 is in fluid communication with the nozzle 102. The liquid reservoir 104 is a reservoir containing ear cleaning solution that is secured to the nozzle 102 to deliver the ear cleaning solution to a user. The liquid reservoir 104 can be a reusable reservoir that a user would fill with ear cleaning solution, or any other suitable liquid. In contrast, the liquid reservoir 104 can be a replacement cartridge 300 (as shown in FIGS. 3A and 3B). A user would take the pre-filled replacement cartridge 300 and remove the lid, usually by unscrewing it. A user then would attach the pre-filled replacement cartridge 300 onto the nozzle 102 and would secure it. Typically, the replacement cartridge 300 would be screwed onto the nozzle 102. Once secure, the pet ear cleaning device 100 would be used as normal.

The pet ear cleaning device 100 further comprises an internal pump assembly and tube 106 that pumps ear cleaning solution or other liquid from the liquid reservoir 104 and transfers it to the nozzle 102. The internal pump assembly and tube 106 functions as a typical pump assembly to pull liquid from the liquid reservoir 104 via the pump tube 106 and transfer it to the nozzle 102 via the pump tube 106. Typically, the liquid reservoir 104 would comprise a manual dispensing component 120 for activating the internal pump assembly and tube 106. The manual dispensing component 120 would comprise a button, a trigger, or a pump, or any other suitable dispensing component as is known in the art without affecting the overall concept of the invention. The button would be simply pressed by a user as many times as needed. A user would press the manual dispensing component 120 which would activate the internal pump assembly which would then draw fluid from the liquid reservoir 104 and transfer it to the nozzle 102.

Further, the pet ear cleaning device 100 would comprise a tip 108 for cleaning the pet's ear. The tip 108 is secured onto the nozzle 102 by pushing the tip 108 vertically down toward the liquid reservoir 104 onto the threads or grip rings positioned on the second end 112 of the nozzle 102, or screwing the tip 108 onto the threads, such that the tip 108 is retained on the nozzle 102. Typically, the tip 108 is cylindrical in shape with a rounded top, however any other suitable shape can be used as is known in the art without affecting the overall concept of the invention, as long as the tip 108 is sized and shaped to fit over the nozzle 102 and to fit in the interior of a pet's ear. Further, the tip 108 would generally be a two part tip with the upper portion or first end 122 constructed of medical grade foam, sterilized cotton, etc., though any other suitable material may be used to manufacture the tip 108 as is known in the art without affecting the overall concept of the invention, and the lower portion or second end 124 would be constructed of a more dense foam, or cotton, to help grip the threads at the base of the nozzle 400. The tip 108 can also comprise a variety of colors, logos, and designs to suit user and manufacturing preference. The tip 108, in its entirety, is approximately between 1.0 and 1.25 inches long as measured from the first end 122 to the second end 124, and approximately between 0.25 and 0.5 inches in diameter. The lower portion of the disposable tip 108 is approximately 0.25 long as measured from end 123 to the second end 124, and has the same diameter as previously mentioned (0.25-0.5 inches).

Once the tip 108 is secured to the nozzle 102, a user presses the manual dispensing component 120 to release fluid from the liquid reservoir 104, which transfers from the liquid reservoir 104 to the nozzle 102. Fluid from the liquid reservoir 104 is then dispensed from the nozzle 102 to the tip 108. The tip 108 retains the fluid which is dispensed from the nozzle 102. Specifically, the nozzle 102 saturates the tip 108 from the inside out by way of a misting action that emanates from the nozzle 102 when the manual dispensing component 120 is activated. A user continues to press the manual dispensing component 120 until the tip 108 is saturated, i.e., the user holds the manual dispensing component 120 down or presses the manual dispensing component 120 up and down, like a pump. Once the tip 108 is saturated, the user releases the manual dispensing component 120 and proceeds with utilizing the saturated tip 108 to clean the pet's ear(s). The saturated tip is not removed from the device 100 during use on a pet's ear(s).

Further, the tip 108 would generally be disposable, thus a user would discard the tip 108 after use and insert a new tip 108 onto the nozzle 102. A user can manually remove the soiled tip 108, or the soiled tip 108 can be removed without a user touching it via a manually operated discard component 101 that allows a user to remove the soiled tip 108 hands free. The manually operated discard component 101 would typically be a button or other lever that a user would press which would act to expel the soiled tip 108, via pushing against the edge of the soiled tip 108 and dislodging it from the threads or grip rings on the nozzle 102.

FIGS. 3A and 3B illustrate the pet ear cleaning device 100 with a replacement cartridge 300. As stated supra, the pet ear cleaning device 100 comprises a liquid reservoir which is secured to the nozzle 102 via any suitable securing means as is known in the art, such as welding, gluing, threading, etc. The liquid reservoir is in fluid communication with the nozzle 102, and contains ear cleaning solution. The liquid reservoir 104 can be a reusable reservoir that a user would re-fill with ear cleaning solution, or any other suitable liquid (as shown in FIGS. 1 and 2). In contrast, the liquid reservoir 104 can be a replacement cartridge 300 (as shown in FIGS. 3A and 3B).

A user would take the pre-filled replacement cartridge 300 and remove the lid, usually by unscrewing it, and then would remove the tamper proof barrier (i.e., foil seal). A user then would attach the pre-filled replacement cartridge 300 onto the nozzle 102 and would secure it, such that the internal pump assembly and tube 106 is encased within the replacement cartridge 300, which allows ear cleaning solution from the replacement cartridge 300 to be transferred to the nozzle 102. Typically, the replacement cartridge 300 would be screwed onto the nozzle 102, but it can be secured to the nozzle 102 via any other suitable securement means as is known in the art without affecting the overall concept of the invention. Once secure, the pet ear cleaning device 100 would be used as normal to clean the pet's ears. Once the replacement cartridge 300 is empty, a user removes the empty cartridge and screws on a new, pre-filled replacement cartridge 300.

FIG. 4 illustrates how the foam tip 108 fits over the nozzle 102 of the pet ear cleaning device 100. As stated supra, the pet ear cleaning device 100 would comprise a tip 108 for cleaning the pet's ear. The tip 108 is secured onto the nozzle 102 by pushing the tip 108 vertically down toward the liquid reservoir 104 onto the threads or grip rings 400 positioned on the second end 112 of the nozzle 102, or by screwing the tip 108 onto the threads, such that the tip 108 is retained on the nozzle 102. The nozzle 102 does not have to comprise threads or grip rings 400, and any suitable retaining mechanism can be used as is known in the art without affecting the overall concept of the invention, such as snap rings, o-rings, etc.

Typically, the tip 108 is cylindrical in shape with a rounded top, however any other suitable shape can be used as is known in the art without affecting the overall concept of the invention, as long as the tip 108 is sized and shaped to fit over the nozzle 102 and to fit in the interior of a pet's ear. Further, the tip 108 would generally be a two part tip with the upper portion or first end 122 constructed of medical grade foam, sterile cotton, etc., though any other suitable material may be used to manufacture the tip 108 as is known in the art without affecting the overall concept of the invention, and the lower portion or second end 124 would be constructed of a more dense foam, or cotton, to help grip the threads at the base of the nozzle 400.

Further, the tip 108 would generally be disposable, thus a user would discard the tip 108 after use and insert a new tip 108 onto the nozzle 102. A user can manually remove the soiled tip 108, or the soiled tip 108 can be removed without a user touching it via a manually operated discard component 101 that allows a user to remove the soiled tip 108 hands free. The manually operated discard component 101 would typically be a button or other lever that a user would press which would act to expel the soiled tip 108, via pushing against the edge of the soiled tip 108 and dislodging it from the threads or grip rings 400 on the nozzle 102.

Figure 5A:
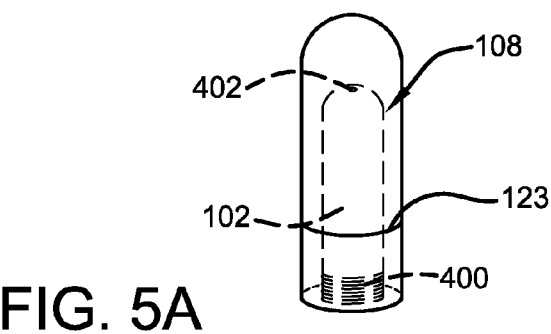
FIGS. 5 A and B illustrate a perspective view of the foam tip and the foam tip soaked with the ear cleaning solution in accordance with the disclosed architecture.

FIGS. 5A and B illustrate the foam tip and the foam tip soaked with the ear cleaning solution. As stated supra, the tip 108 is secured onto the nozzle 102, and once the tip 108 is secured to the nozzle 102, a user presses the manual dispensing component 120 to release fluid from the liquid reservoir 104, which transfers from the liquid reservoir 104 to the nozzle 102. Fluid from the liquid reservoir 104 is then dispensed from the nozzle 102 to the tip 108. The tip 108 retains the fluid which is dispensed from the nozzle 102. Specifically, an opening(s) 402 in the nozzle 102 release the fluid from the liquid reservoir 104 and saturate the tip 108 from the inside out by way of a misting action that emanates from the nozzle 102 when the manual dispensing component 120 is activated.

Figure 5B:
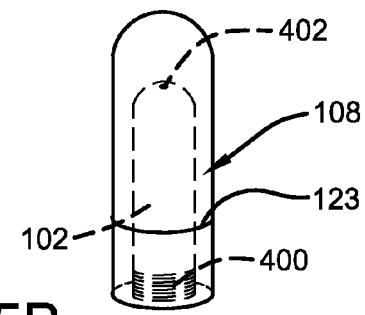

The manual dispensing component 120 can comprise a button, a trigger, or a pump, or any other suitable dispensing component as is known in the art without affecting the overall concept of the invention. The button would simply be pressed by a user as many times as needed. A user would press the manual dispensing component 120 which would activate the internal pump assembly which would then draw fluid from the liquid reservoir and transfer it to the nozzle. A user continues to press the manual dispensing component 120 until the tip 108 is saturated, i.e., the user holds the manual dispensing component 120 down or presses the manual dispensing component 120 up and down, like a pump. Once the tip 108 is saturated (as shown in FIG. 5B), the user releases the manual dispensing component 120 and proceeds with utilizing the saturated tip 108 to clean the pet's ear(s). The saturated tip is not removed from the device 100 during use on a pet's ear(s).

Figure 6:
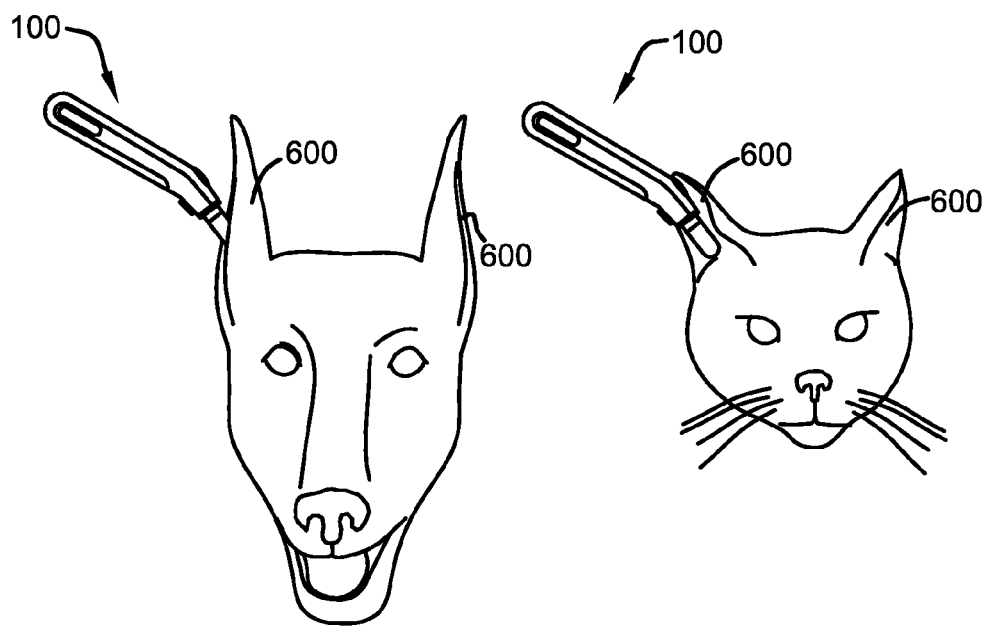
FIG. 6 illustrates a perspective view of the pet ear cleaning device in use in accordance with the disclosed architecture.

FIG. 6 illustrates the pet ear cleaning device 100 in use. In operation, a user (not shown) would choose a pet ear cleaning device 100. The user would then either fill up the liquid reservoir 104 with ear cleaning solution or would unscrew the cap of a pre-filled replacement cartridge 300 and then would secure the filled liquid reservoir 104 or replacement cartridge 300 to the nozzle 102. Typically, the user would screw on the liquid reservoir 104 or replacement cartridge 300 directly onto the nozzle 102. Once the liquid reservoir 104 or replacement cartridge 300 is secured to the nozzle 102, the user then removes the dust cap 114 from the nozzle 102 and replaces it with a foam tip 108. The user then inserts the foam tip 108 over the nozzle 102 of the pet ear cleaning device 100, and secures it onto the nozzle 102 by pushing the tip 108 vertically down toward the liquid reservoir 104 onto the threads or grip rings 400 positioned on the second end 112 of the nozzle 102, such that the tip 108 is retained on the nozzle 102

Once the foam tip 108 is secured to the nozzle 102, the user presses the manual dispensing component 120 which would activate the internal pump assembly which would then draw fluid from the liquid reservoir 104 and transfer it to the nozzle 102. Fluid from the liquid reservoir 104 is then dispensed from the nozzle 102 to the tip 108. The tip 108 retains the fluid which is dispensed from the nozzle 102. Specifically, the nozzle 102 saturates the tip 108 from the inside out by way of a misting action that emanates from the nozzle 102 when the manual dispensing component 120 is activated. The user continues to press the manual dispensing component 120 until the tip 108 is saturated, i.e., the user holds the manual dispensing component 120 down or presses the manual dispensing component 120 up and down, like a pump. Once the tip 108 is saturated, the user releases the manual dispensing component 120 and proceeds with utilizing the saturated tip 108 to clean the pet's ear(s) 600. The saturated tip 108 is not removed from the device 100 during use on a pet's ear(s).

Furthermore, the tip 108 is disposable, thus a user would discard the tip 108 after use and insert a new tip 108 onto the nozzle 102. The user would manually remove the soiled tip 108, or the soiled tip 108 would be removed without the user touching it via a manually operated discard component 101 that allows the user to remove the soiled tip 108 hands free. The manually operated discard component 101 would typically be a button or other lever that the user would press which would act to expel the soiled tip 108, via pushing against the edge of the soiled tip 108 and dislodging it from the threads or grip rings 400 on the nozzle 102. Once the soiled tip 108 is removed, the user inserts a new tip 108 and continues cleaning the pet's ear(s) 600. If the user is done cleaning the pet's ear(s) 600, the user removes the soiled tip 108 and covers the nozzle 102 with the dust cap 114 and stores the device 100.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A pet ear cleaning device, comprising:
    a hollow nozzle comprising an interior tube and a first end and a second end;
    a liquid reservoir comprising a first end and a second end, and in fluid communication with the hollow nozzle, wherein the first end of the liquid reservoir is secured to the second end of the hollow nozzle;
    an internal pump assembly in fluid communication with the interior tube of the hollow nozzle for transferring fluid from the liquid reservoir to the hollow nozzle;
    a manual dispensing component for activating the internal pump assembly;
    a two part tip for cleaning a pet's ear secured to the first end of the hollow nozzle, and comprising a first end constructed of medical grade foam and a second end constructed of more dense foam; wherein the hollow nozzle comprises a plurality of threads at a base of the hollow nozzle to secure the two part tip on the hollow nozzle;
    a manually operated discard component that removes a soiled tip hands free; and
    a dust cap to protect the hollow nozzle when the device is not in use;
    wherein during use, the two part tip is secured to the hollow nozzle via the plurality of threads; and when the device is not in use, the two part tip is discarded and the dust cap is secured to the hollow nozzle via the plurality of threads.

2. The pet ear cleaning device of claim 1, wherein the two part tip is a two part disposable tip.

3. The pet ear cleaning device of claim 2, wherein the two part disposable tip retains fluid which is dispensed from the hollow nozzle.

4. The pet ear cleaning device of claim 3, wherein the hollow nozzle saturates the two part tip from inside out by way of a misting action that emanates from the hollow nozzle when the manual dispensing component is activated.

5. The pet ear cleaning device of claim 1, wherein the manual dispensing component is at least one of a button, a trigger, or a pump.

6. The pet ear cleaning device of claim 1, wherein the liquid reservoir is a replacement cartridge that is secured to the hollow nozzle.

7. The pet ear cleaning device of claim 6, wherein the fluid in the liquid reservoir is ear cleaning solution.

8. A pet ear cleaning device, comprising:
    a hollow nozzle comprising an interior tube and a first end and a second end, and grip rings at a base of the hollow nozzle;
    a liquid reservoir comprising a first end and a second end, and in fluid communication with the hollow nozzle, wherein the first end of the liquid reservoir is secured to the second end of the hollow nozzle;
    an internal pump assembly in fluid communication with the interior tube of the hollow nozzle for transferring fluid from the liquid reservoir to the hollow nozzle;
    a manual dispensing component for activating the internal pump assembly; and
    a two part disposable tip for cleaning a pet's ear secured to the first end of the hollow nozzle, and comprising a first end constructed of medical grade foam and a second end constructed of more dense foam;
    a manually operated discard component that removes a soiled tip hands free; and
    wherein the grip rings at the base of the hollow nozzle secure the two part disposable tip on the hollow nozzle; and
    a dust cap to protect the hollow nozzle when the device is not in use;
    wherein during use, the two part tip is secured to the hollow nozzle via the grip rings; and
    when the device is not in use, the two part tip is discarded and the dust cap is secured to the hollow nozzle via the grip rings.

9. The pet ear cleaning device of claim 8, wherein the two part disposable tip retains fluid which is dispensed from the hollow nozzle.

10. The pet ear cleaning device of claim 9, wherein the hollow nozzle saturates the two part disposable tip from inside out by way of a misting action that emanates from the hollow nozzle when the manual dispensing component is activated.

11. The pet ear cleaning device of claim 8, wherein the manual dispensing component is at least one of a button, a trigger, or a pump.

12. The pet ear cleaning device of claim 8, wherein the liquid reservoir is a replacement cartridge that is secured to the hollow nozzle.

13. A pet ear cleaning device, comprising:
    a hollow nozzle comprising an interior tube and a first end and a second end, and grip rings at a base of the hollow nozzle;
    a replacement cartridge comprising a first end and a second end, and in fluid communication with the hollow nozzle, wherein the first end of the replacement cartridge is secured to the second end of the hollow nozzle;

an internal pump assembly in fluid communication with the interior tube of the hollow nozzle for transferring fluid from the replacement cartridge to the hollow nozzle;

a manual dispensing component for activating the internal pump assembly; and a two part disposable tip for cleaning a pet's ear secured to the first end of the hollow nozzle, and comprising a first end constructed of medical grade foam and a second end constructed of more dense foam; and a manually operated discard component that removes a soiled tip hands free; and wherein the grip rings at the base of the hollow nozzle secure the two part disposable tip on the hollow nozzle; and a dust cap to protect the hollow nozzle when the device is not in use;

wherein during use, the two part tip is secured to the hollow nozzle via the grip rings; and when the device is not in use, the two part tip is discarded and the dust cap is secured to the hollow nozzle via the grip rings.

14. The pet ear cleaning device of claim 13, wherein the replacement cartridge is secured to the hollow nozzle via threads, and then un-threaded and removed once empty, and replaced with a new, filled replacement cartridge.

15. The pet ear cleaning device of claim 13, wherein the manual dispensing component is at least one of a button, a trigger, or a pump.

* * * * *